United States Patent
Smith et al.

(10) Patent No.: US 6,297,046 B1
(45) Date of Patent: Oct. 2, 2001

(54) MULTILAYER GAS-PERMEABLE CONTAINER FOR THE CULTURE OF ADHERENT AND NON-ADHERENT CELLS

(75) Inventors: Sidney T. Smith, Lake Forest; David V. Bacehowski, Wildwood; William Kolanko, Grayslake; Larry Rosenbaum, Gurnee; Stephen L. Smith, Arlington Heights; James G. Bender, Lindenhurst; Lecon Woo, Libertyville; Michael T. K. Ling, Vernon Hills, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/330,717

(22) Filed: Oct. 28, 1994

(51) Int. Cl.$^7$ .................................................. C12M 3/06
(52) U.S. Cl. .................... 435/297.5; 435/401; 435/304.1
(58) Field of Search ............................. 435/288.1, 288.2, 435/292.1, 297.1, 297.5, 304.1–304.3, 401; 428/35.7, 213–216, 332–336; 525/66; 383/100, 102; 206/484, 484.1, 484.2; 604/408

(56) References Cited

U.S. PATENT DOCUMENTS

| | | |
|---|---|---|
| D. 285,725 | 9/1986 | Franchere . |
| 2,705,223 | 3/1955 | Renfrew et al. ........................ 260/18 |
| 2,990,306 * | 6/1961 | Dyer ..................................... 154/2.65 |
| 3,255,923 | 6/1966 | Soto ........................................ 222/80 |
| 3,375,300 | 3/1968 | Ropp ..................................... 260/857 |
| 3,419,654 | 12/1968 | Chiba et al. ........................... 264/210 |
| 3,485,782 | 12/1969 | Nagle ...................................... 260/27 |
| 3,589,976 * | 6/1971 | Erb ........................................ 428/216 |
| 3,655,503 * | 4/1972 | Stanley et al. ........................ 156/272 |
| 3,661,674 | 5/1972 | Higgs et al. .......................... 156/280 |
| 3,772,136 | 11/1973 | Workman ............................... 161/169 |
| 3,885,081 | 5/1975 | Van Paesschen et al. ........... 428/474 |
| 3,912,843 | 10/1975 | Brazier ................................. 428/474 |
| 3,937,758 | 2/1976 | Castagna . |
| 3,960,997 | 6/1976 | Sorensen ................................ 264/40 |
| 3,995,084 | 11/1976 | Berger et al. ........................... 428/35 |

(List continued on next page.)

FOREIGN PATENT DOCUMENTS

| | | |
|---|---|---|
| 2800437 | 7/1978 | (DE) . |
| 4142271 | 6/1993 | (DE) . |
| 092897 | 2/1983 | (EP) . |

(List continued on next page.)

OTHER PUBLICATIONS

Polymer Handbook, 3rd. Ed., J. Brandrup and E.H. Immergut, John Wiley & Sons. Date Unknown.

Encyclopedia of Polymer Science and Engineering, Date Unknown vol. 16, Styrene, Polymers to Toys, John Wiley & Sons.

Toughened Plastics, C.B. Bucknall, Applied Science Publishers, Ltd. Date Unknown.

Polymer Blends, vol. 1, Seymour Newman, Academic Press. Date Unknown.

Thermoplastics for Health–Care Products: Clear Choices Are Not So Clear, K.Z. Hong, Ph.D., Baxter Healthcare Corporation. Date Unknown.

Plastics Engineering, Oct., 1995, Official Publication of The Society of Plastics Engineering. Date Unknown.

*Primary Examiner*—William H. Beisner
(74) *Attorney, Agent, or Firm*—Mark J Buonaiuto; Joseph A Fuchs

(57) ABSTRACT

A multi-layer, flexible, gas-permeable film (10) suitable for forming a cell culture container (20), the film (10) comprising a first layer (12) composed of a polystyrene having a thickness within the range of 0.0001 inches to about 0.0010 inches and, a second layer (14) adhered to the first layer (12) composed of a polyolefin having a thickness within the range of 0.004 inches to about 0.015 inches.

42 Claims, 3 Drawing Sheets

U.S. PATENT DOCUMENTS

| | | |
|---|---|---|
| 4,005,710 | 2/1977 | Zeddies et al. . |
| 4,041,103 | 8/1977 | Davison et al. . |
| 4,045,515 | 8/1977 | Isaka et al. .......................... 260/897 |
| 4,058,647 | 11/1977 | Inoue et al. . |
| 4,085,244 | 4/1978 | Stillman ............................... 428/192 |
| 4,087,587 | 5/1978 | Shida et al. ......................... 428/500 |
| 4,087,588 | 5/1978 | Shida et al. ......................... 428/500 |
| 4,095,012 | 6/1978 | Schirmer ............................. 428/474 |
| 4,103,686 | 8/1978 | LeFevre . |
| 4,112,989 | 9/1978 | Grode et al. ............................ 150/1 |
| 4,140,162 | 2/1979 | Gajewski et al. ........................ 150/1 |
| 4,147,827 | 4/1979 | Breidt, Jr. et al. . |
| 4,156,709 | 5/1979 | Kondo et al. ........................ 264/171 |
| 4,161,362 | 7/1979 | Blake ................................... 355/40 |
| 4,188,350 | 2/1980 | Vicik et al. .......................... 525/232 |
| 4,226,822 | 10/1980 | Yoshikawa et al. ................. 264/173 |
| 4,227,527 | 10/1980 | DeFrank et al. ..................... 128/214 |
| 4,230,830 | 10/1980 | Tanny et al. . |
| 4,233,367 | 11/1980 | Ticksor ............................... 428/476 |
| 4,244,378 | 1/1981 | Brignola . |
| 4,261,473 | 4/1981 | Yamada et al. ........................ 215/1 |
| 4,274,900 | 6/1981 | Mueller et al. ...................... 156/229 |
| 4,286,628 | 9/1981 | Paradis et al. . |
| 4,294,935 | 10/1981 | Kodera et al. ........................ 525/60 |
| 4,310,017 | 1/1982 | Raines . |
| 4,311,807 | 1/1982 | McCullough, Jr. et al. . |
| 4,322,465 | 3/1982 | Webster ............................... 428/194 |
| 4,322,480 | 3/1982 | Tuller et al. ......................... 428/476 |
| 4,327,726 | 5/1982 | Kwong et al. ....................... 128/272 |
| 4,332,655 | 6/1982 | Berejka . |
| 4,333,968 | 6/1982 | Nahmias ............................. 427/173 |
| 4,362,844 | 12/1982 | Lemstra et al. ....................... 525/57 |
| 4,369,812 | 1/1983 | Paradis et al. . |
| 4,387,184 | 6/1983 | Coquard et al. ..................... 525/183 |
| 4,405,667 | 9/1983 | Christensen et al. . |
| 4,407,877 | 10/1983 | Rasmussen . |
| 4,407,888 | 10/1983 | Crofts ................................... 428/355 |
| 4,417,753 | 11/1983 | Bacehowski et al. ................. 285/21 |
| 4,421,235 | 12/1983 | Moriya ................................ 206/524 |
| 4,429,076 | 1/1984 | Saito et al. ............................ 525/57 |
| 4,440,824 * | 4/1984 | Bonis ................................... 428/216 |
| 4,464,439 * | 8/1984 | Castelein ............................ 428/35.7 |
| 4,479,989 | 10/1984 | Mahal .................................. 428/35 |
| 4,497,857 | 2/1985 | Bonis . |
| 4,514,499 | 4/1985 | Noll . |
| 4,521,437 | 6/1985 | Storms ................................. 426/130 |
| 4,540,537 | 9/1985 | Kamp .................................. 264/171 |
| 4,546,085 | 10/1985 | Johansson et al. . |
| 4,548,348 | 10/1985 | Clements . |
| 4,562,118 | 12/1985 | Marchashi et al. .................. 428/412 |
| 4,568,333 | 2/1986 | Sawyer et al. . |
| 4,568,723 | 2/1986 | Lu . |
| 4,572,854 | 2/1986 | Dallmann et al. ..................... 428/35 |
| 4,588,648 | 5/1986 | Krueger et al. ...................... 428/475 |
| 4,599,276 | 7/1986 | Martini . |
| 4,614,781 | 9/1986 | Hori et al. ........................ 525/330.6 |
| 4,621,014 | 11/1986 | Lu ........................................ 428/216 |
| 4,627,844 | 12/1986 | Schmitt ................................ 604/264 |
| 4,636,412 | 1/1987 | Field ..................................... 428/35 |
| 4,640,870 | 2/1987 | Akazawa et al. . |
| 4,643,926 | 2/1987 | Mueller ................................. 428/35 |
| 4,654,240 | 3/1987 | Johnston ............................... 428/35 |
| 4,678,713 | 7/1987 | Lancaster et al. ................... 428/421 |
| 4,680,208 | 7/1987 | Aoki et al. ............................ 428/35 |
| 4,683,916 | 8/1987 | Raines . |
| 4,684,364 | 8/1987 | Sawyer et al. . |
| 4,686,125 | 8/1987 | Johnston et al. . |
| 4,690,915 | 9/1987 | Rosenberg . |
| 4,692,361 | 9/1987 | Johnston et al. . |
| 4,705,708 | 11/1987 | Briggs et al. . |
| 4,707,389 | 11/1987 | Ward ..................................... 428/36 |
| 4,717,668 * | 1/1988 | Keilman et al. ..................... 435/296 |
| 4,722,725 | 2/1988 | Sawyer et al. . |
| 4,724,028 | 2/1988 | Zabielski et al. .................... 156/256 |
| 4,724,961 | 2/1988 | Shimoyamada et al. ........... 206/439 |
| 4,726,997 | 2/1988 | Mueller et al. . |
| 4,732,795 | 3/1988 | Ohya et al. . |
| 4,734,327 | 3/1988 | Vicik .................................... 428/332 |
| 4,735,855 | 4/1988 | Wofford et al. ...................... 428/349 |
| 4,740,582 | 4/1988 | Coquard et al. .................. 528/339.3 |
| 4,753,222 | 6/1988 | Morishita ................................. 128/4 |
| 4,760,114 | 7/1988 | Haaf et al. . |
| 4,764,404 | 8/1988 | Genske et al. ......................... 428/35 |
| 4,767,651 | 8/1988 | Starczewski et al. ................. 428/35 |
| 4,769,262 * | 9/1988 | Ferrar et al. ....................... 428/35.7 |
| 4,770,856 | 9/1988 | Uthemann et al. .................. 422/104 |
| 4,772,497 | 9/1988 | Maasola ................................. 428/35 |
| 4,778,697 | 10/1988 | Genske et al. ......................... 428/35 |
| 4,792,488 | 12/1988 | Schirmer . |
| 4,795,782 | 1/1989 | Lutz et al. . |
| 4,800,129 | 1/1989 | Deak ................................. 428/474.4 |
| 4,801,484 | 1/1989 | Yao et al. ............................. 428/294 |
| 4,803,102 | 2/1989 | Raniere et al. ..................... 428/35.2 |
| 4,824,720 | 4/1989 | Malone ............................... 428/294 |
| 4,829,002 | 5/1989 | Pattillo et al. ....................... 435/284 |
| 4,834,755 | 5/1989 | Silvestrini et al. .................... 623/13 |
| 4,839,292 | 6/1989 | Cremonese ......................... 435/313 |
| 4,855,356 | 8/1989 | Holub et al. . |
| 4,856,259 | 8/1989 | Woo et al. . |
| 4,856,260 | 8/1989 | Woo et al. . |
| 4,863,996 | 9/1989 | Nakazima et al. . |
| 4,871,799 | 10/1989 | Kobayashi et al. .................... 525/64 |
| 4,873,287 | 10/1989 | Holub et al. . |
| 4,877,682 | 10/1989 | Sauers et al. ........................ 428/412 |
| 4,879,232 | 11/1989 | MacDonald et al. . |
| 4,885,119 | 12/1989 | Mueller et al. . |
| 4,910,085 | 3/1990 | Raniere et al. ...................... 428/412 |
| 4,910,147 | 3/1990 | Bacehowski et al. ............... 435/296 |
| 4,915,893 | 4/1990 | Gogolewski et al. ............... 264/205 |
| 4,923,470 | 5/1990 | Dumican ............................... 623/11 |
| 4,929,479 | 5/1990 | Shishido et al. .................... 428/35.2 |
| 4,937,194 | 6/1990 | Pattillo et al. ....................... 435/240 |
| 4,939,151 | 7/1990 | Bacehowski et al. ............... 435/284 |
| 4,948,643 | 8/1990 | Mueller . |
| 4,957,966 | 9/1990 | Nishio et al. . |
| 4,957,967 | 9/1990 | Mizuno et al. . |
| 4,966,795 | 10/1990 | Genske et al. ...................... 428/34.3 |
| 4,968,624 | 11/1990 | Bacehowski et al. . |
| 4,977,213 | 12/1990 | Giroud-Abel et al. ................ 525/66 |
| 4,978,579 | 12/1990 | Rosenbaum ......................... 428/483 |
| 4,996,054 | 2/1991 | Pietsch et al. ....................... 424/422 |
| 4,999,254 | 3/1991 | Ofstein . |
| 4,999,297 | 3/1991 | Minoura et al. ..................... 435/240 |
| 5,006,114 | 4/1991 | Rogers et al. . |
| 5,006,601 | 4/1991 | Lutz et al. . |
| 5,017,490 | 5/1991 | Van Taiariol et al. ............... 435/240 |
| 5,017,652 | 5/1991 | Abe et al. . |
| 5,034,457 | 7/1991 | Serini et al. . |
| 5,034,458 | 7/1991 | Serini et al. . |
| 5,037,754 * | 8/1991 | Tanaka et al. ....................... 435/296 |
| 5,053,457 | 10/1991 | Lee . |
| 5,066,290 | 11/1991 | Measells et al. . |
| 5,071,686 | 12/1991 | Genske et al. . |
| 5,071,911 | 12/1991 | Furuta et al. . |
| 5,071,912 | 12/1991 | Furuta et al. . |
| 5,075,376 | 12/1991 | Furuta et al. . |
| 5,079,295 | 1/1992 | Furuta et al. . |
| 5,085,649 | 2/1992 | Flynn .................................. 604/282 |
| 5,093,164 | 3/1992 | Bauer et al. . |
| 5,093,194 | 3/1992 | Touhsaent et al. . |
| 5,094,921 | 3/1992 | Itamura et al. . |

| | | |
|---|---|---|
| 5,098,202 | 3/1992 | Rosenbaum ............................ 383/67 |
| 5,108,844 | 4/1992 | Blemberg et al. . |
| 5,110,642 | 5/1992 | Genske . |
| 5,116,906 | 5/1992 | Mizuno et al. . |
| 5,126,132 | 6/1992 | Rosenberg . |
| 5,127,904 | 7/1992 | Loo et al. . |
| 5,129,894 | 7/1992 | Sommermeyer et al. ........... 604/408 |
| 5,132,363 | 7/1992 | Furuta et al. . |
| 5,135,785 | 8/1992 | Millon . |
| 5,139,831 | 8/1992 | Mueller . |
| 5,139,946 | 8/1992 | Howell et al. ....................... 435/240 |
| 5,145,731 | 9/1992 | Lund et al. . |
| 5,154,979 | 10/1992 | Kerschbaumer et al. . |
| 5,159,004 | 10/1992 | Furuta et al. . |
| 5,164,267 | 11/1992 | D'Heur et al. . |
| 5,164,268 | 11/1992 | Dollinger et al. ................ 428/476.3 |
| 5,176,634 | 1/1993 | Smith et al. ........................... 604/87 |
| 5,176,956 | 1/1993 | Jevne et al. .......................... 128/640 |
| 5,183,706 | 2/1993 | Bekele . |
| 5,185,189 | 2/1993 | Stenger et al. . |
| 5,189,091 | 2/1993 | Laughner . |
| 5,190,879 * | 3/1993 | Wolfe et al. ......................... 435/287 |
| 5,194,316 | 3/1993 | Horner et al. . |
| 5,196,254 | 3/1993 | Akiyama . |
| 5,206,290 | 4/1993 | Mizuno et al. . |
| 5,212,238 | 5/1993 | Scheibelhoffer et al. . |
| 5,218,048 | 6/1993 | Abe et al. . |
| 5,225,346 | 7/1993 | Matsumiya et al. ................. 435/284 |
| 5,230,934 | 7/1993 | Sakano et al. . |
| 5,230,935 | 7/1993 | Delimoy et al. . |
| 5,238,997 | 8/1993 | Bauer et al. . |
| 5,244,971 | 9/1993 | Jean-Marc . |
| 5,258,230 | 11/1993 | LaFleur et al. . |
| 5,272,084 | 12/1993 | O'Connell et al. ................... 435/240 |
| 5,278,231 | 1/1994 | Chundury .............................. 525/66 |
| 5,288,531 | 2/1994 | Falla et al. . |
| 5,288,799 | 2/1994 | Schmid et al. . |
| 5,290,856 | 3/1994 | Okamoto et al. . |
| 5,306,542 | 4/1994 | Bayer . |
| 5,310,676 | 5/1994 | Johansson et al. . |
| 5,312,867 | 5/1994 | Mitsuno et al. . |
| 5,317,059 | 5/1994 | Chundury et al. . |
| 5,342,886 | 8/1994 | Glotin et al. . |
| 5,348,794 | 9/1994 | Takahashi et al. . |
| 5,356,676 | 10/1994 | von Widdern et al. . |
| 5,356,709 | 10/1994 | Woo et al. . |
| 5,371,141 | 12/1994 | Gelles et al. . |
| 5,378,543 | 1/1995 | Murata et al. . |
| 5,378,800 | 1/1995 | Mok et al. . |
| 5,387,645 | 2/1995 | Montag et al. . |

FOREIGN PATENT DOCUMENTS

| | | |
|---|---|---|
| 310143 | 7/1985 | (EP) . |
| 148161 | 10/1985 | (EP) . |
| 340305 | 1/1988 | (EP) . |
| 446505 | 3/1990 | (EP) . |
| 194684 | 3/1991 | (EP) . |
| 0447953 * | 9/1991 | (EP) ..................................... 428/336 |
| 488544 A1 | 3/1992 | (EP) . |
| 552412 A1 | 7/1993 | (EP) . |
| 2688511 | 3/1992 | (FR) . |
| 1059554 | 2/1967 | (GB) . |
| 2094832 | 9/1982 | (GB) . |
| 2177974 | 2/1987 | (GB) . |
| 5338089 * | 12/1983 | (JP) ..................................... 428/35.7 |
| 59-83651 * | 5/1984 | (JP) . |
| 63-110150 * | 5/1988 | (JP) . |
| 1-291171 | 11/1989 | (JP) . |
| 3 065 177 | 3/1991 | (JP) . |
| 86/07010 | 12/1986 | (WO) . |
| 90/03427 | 4/1990 | (WO) . |
| WO 91/09719 | 7/1991 | (WO) . |
| 83/00158 | 1/1993 | (WO) . |
| WO 93/02859 | 2/1993 | (WO) . |
| 93/09718 | 5/1993 | (WO) . |
| 93/23093 | 11/1993 | (WO) . |

* cited by examiner

MULTILAYER GAS-PERMEABLE CONTAINER FOR THE CULTURE OF ADHERENT AND NON-ADHERENT CELLS

TECHNICAL FIELD

This invention relates to multi-layer films, and containers formed therefrom for the in vitro culture of cells. Specifically, the invention is directed to a multi-layer, flexible, gas permeable container having an inner growing surface of polystyrene, which is conducive to the culture of cells.

BACKGROUND ART

There are two major types of cells grown in vitro: suspension cells (anchorage-independent cells); and adherent cells (anchorage-dependent cells). Suspension or anchorage-independent cells can multiply, in vitro, without being attached to a surface. In contrast, adherent cells require attachment to a surface in order to grow in vitro. Additionally, some non-adherent cells grow best on a surface that promotes adherent cell growth.

It is known to grow adherent cells, in vitro, in polystyrene flasks. Polystyrene is the most common type of plastic used in the manufacture of rigid, gas impermeable cell culture flasks or plates. It is thought that polystyrene promotes the growth of adherent cells because of its ability to maintain electrostatic charges on its surface which attract oppositely charged proteins on the cell surfaces. However, to date, the available polystyrene culture containers have been of the rigid flask or plate type because polystyrene is known in the art as a rigid, gas-impermeable plastic.

Cells are commonly cultured in a growth medium within polystyrene or other containers placed in enclosed incubators. In addition to providing a certain degree of isolation from pathogens, the incubators maintain a constant temperature, usually 37° C., and a constant gas mixture. The gas mixture must be optimized for a given cell type, and be controlled for at least two parameters: (1) partial pressure of oxygen ($pO_2$) to serve the aerobic needs of the cells, and (2) partial pressure of carbon dioxide ($pCO_2$) to maintain the pH of the growth medium. Since the known types of rigid cell culture containers are gas impermeable, their lids or caps are not sealed onto the containers. Rather, they are offset sufficiently to allow gas exchange through a gap or vent between the cap and the container. Such a container is disadvantageous for clinical uses because the vent might allow contamination of the culture or lead to accidents involving biohazardous agents.

In addition to polystyrene flasks, others have constructed flexible, breathable containers for containing adherent cells to be grown in vitro. For example, the commonly assigned U.S. Pat. No. 4,939,151 provides a gas-permeable bag with at least one access port. This allows for a closed system (ie., one without a vent). The bag disclosed in the '151 Patent is constructed from two side walls. The first side wall is made of ethylene-vinyl acetate ("EVA") which may be positively or negatively charged. The second side wall is constructed from a gas permeable film such as ethylene-vinyl acetate or a polyolefin. The first side wall is sealed to the second side wall along their edges. While EVA can hold an electrostatic charge, the charge has the undesirable tendency to decay over time. Eventually, the decay will render the container ineffective for growing adherent cells.

It has been found that the cell growth rate within a sealed container may be influenced by the gas permeability characteristics of the container walls. The optimal gas requirements, however, vary by cell type and over the culture period. Thus, it is desirable to be able to adjust the gas permeability of the container. The polystyrene flask, and the flexible flask which is entirely constructed from a monofilm, do not provide for such adjustability.

SUMMARY OF THE INVENTION AND OBJECTS

The present invention provides a multi-layer, co-extruded film suitable for producing gas-permeable cell culture bags. The film has an ultra-thin first layer of polystyrene having a thickness from about 0.0001 inches to about 0.0010 inches. The film has second layer adhered to the first layer made of a polyolefin. The polyolefin acts as a flexible substrate for the polystyrene to provide a flexible, gas permeable film. Thus, the second layer is sometimes referred to as the substrate layer.

The film may also have an adhesive tie layer interposed between the first and second layers. The film may also have one or more additional outer layers of polyolefin (such as polypropylene) to provide strength and scratch resistance, as well as additional tie layers interposed between these additional layers.

The film most preferably has the following physical characteristics: (1) a mechanical modulus of between about 10,000 and 30,000 psi (ASTM D 790); (2) an oxygen permeability within the range of about 9–15 Barrers; (3) a carbon dioxide permeability of 40–80 Barrers; (4) a nitrogen permeability of 10–100 Barrers, and (5) a water vapor transmission rate of not more than 20 (g mil/100 in$^2$/day). Preferably, the film should have an optical clarity of between about 0.1% to about 10% as measured by a Hazometer in accordance with ASTM D1003.

The present invention also provides a flexible, gas-permeable cell culture container constructed from the above described films, with the polystyrene layer forming the inner surface of the container.

Another aspect of the present invention provides a flexible, gas-permeable cell culture container whose gas permeability may be adjusted to best match the requirements of the cell being cultured in the container. The multi-layer structure of the present film allows one to vary the material of the second layer or substrate layer and its thickness to achieve the desired or predetermined gas permeability requirements for cell growth. Preferably, the type and thickness of the substrate layer will be selected to optimize cell growth.

Another aspect of the invention provides for various embodiments of culture containers some of which are advantageous for growing adherent cells, non-adherent cells, and both.

Another aspect of the invention is to provide a flexible, gas permeable cell culture container having a first side that is suitable for growing adherent cells, a second side for growing non-adherent cells, and indicia on the container for indicating the first side from the second side.

DETAILED DESCRIPTION OF THE INVENTION

The present invention provides a multi-layer, gas-permeable flexible film, having a surface layer formed of polystyrene, and a cell culture container constructed therefrom, having an inner surface of polystyrene.

I. The Film Components

Figure 1:
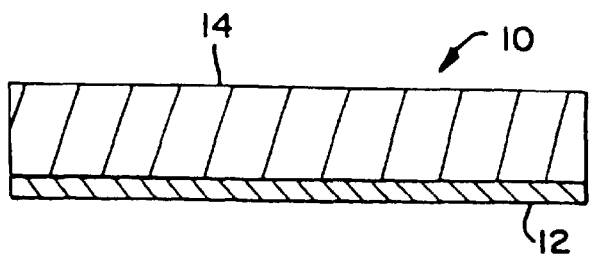
FIG. 1 is a cross-sectional view of a two-layer, gas-permeable, flexible film of the invention.
Figure 2:
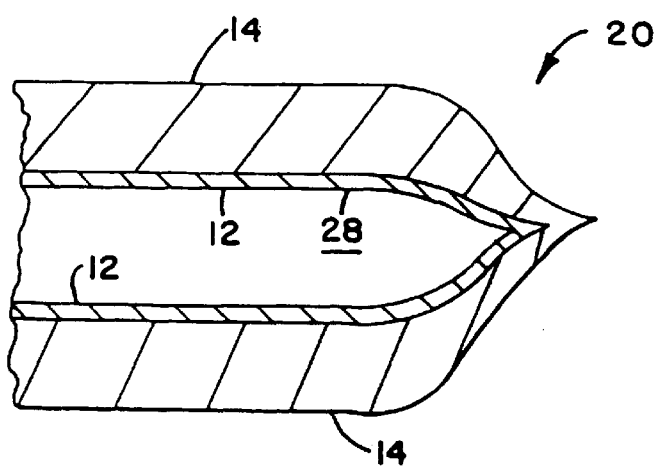
FIG. 2 is a cross-sectional view of the flexible, gas-permeable cell culture container of the invention.

FIG. 1 shows a two-layer film 10, of which the first layer 12 of the film forms an inner cell growth surface when fabricated into a cell culture container 20 (FIG. 2). The film 10 having an effective thickness to allow cell culture growth. The first layer 12 is an ultra-thin layer of polystyrene, preferably having a thickness from about 0.0001 inches to about 0.0010 inches, more preferably 0.0002 inches to about 0.0006 inches, and most preferably about 0.0003 inches. The polystyrene material may be selected from, but not limited to, polystyrenes such as high impact polystyrenes ("HIPS") which are a general purpose polystyrene modified by polybutadiene rubber. Such a polystyrene is sold by Dow Chemical Company under the product designation Styron 47827, Natural.

The second layer 14 is composed of a polyolefin. Preferably, the polyolefin includes a polymer alloy comprising three components: styrene-ethylene-butadiene-styrene ("SEBS") block copolymer (40%–85% by weight), ethylene vinyl acetate (0–40% by weight), and polypropylene (10%–40% by weight) as described in the commonly assigned U.S. Pat. No. 4,140,162 which is incorporated herein by reference. Such a polymer alloy is sold by Baxter International Inc. under the product designation PL-732®.

It is also desirable to use, for the second layer 14, other three and four component polymer alloys such as those disclosed in co-pending, and commonly assigned patent application Ser. No. 08/153,823 which is incorporated herein by reference. One such group of polymer alloys consists of a first component of a polypropylene which constitutes approximately 30–60% by weight of the polymer alloy. The second component is preferably an ultra low density polyethylene or polybutene-1 which constitute approximately 25–50% by weight of the polymer alloy. The third component of the polymer alloy is preferably a dimer fatty acid polyamide (which should be interpreted to include their hydrogenated derivatives as well), which constitutes approximately 5–40% by weight of the polymer alloy. The fourth component is a compatibilizing polymer that may be selected from various block copolymers of styrene with dienes or alpha olefins; the compatibilizing polymers may be modified with minor amounts of chemically active functionalities such as maleic anhydride. For example, the compatibilizing polymer may be an SEBS block copolymers. The fourth component should constitute between 5–40% by weight of the polymer alloy.

Preferably, the second layer 14, (which may sometimes be referred to as the substrate layer 14) has a thickness within a range of about 0.004 inches to about 0.015 inches, more preferably 0.005 inches to about 0.012 inches, and most preferably 0.006 inches to about 0.008 inches.

In another embodiment of the invention (FIG. 3), the film may include a first tie layer 16 interposed between the first and second layers 12 and 14. Preferably the first tie layer is a gas permeable olefin and more preferably an ethylene polymer containing vinyl acetate within the range of 16%–30% by weight and most preferably ethylene vinyl acetate with 28% vinyl acetate. Other examples of these polymers include those sold by Quantum Chemicals under the trade name Bynel. It is also possible to use SEBS block copolymers as the first tie layer such as those sold by Shell Chemical Company under the tradename Kraton.

The first tie layer 16 adheres the first layer 12 to the second layer 14. The first tie layer 16 has a thickness preferably within a range from about 0.0002 inches to about 0.0012 inches, more preferably from about 0.0004 inches to about 0.0010 inches, and most preferably about 0.0005 inches.

Figure 3:
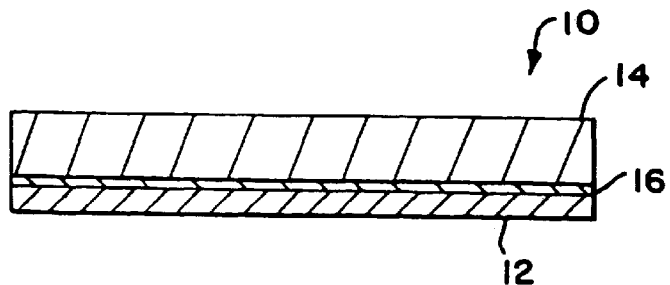
FIG. 3 is a cross-sectional view of a three-layer, gas-permeable, flexible film of the invention.

In yet another embodiment of the invention (FIG. 4), the film shown in FIG. 3 may also have a skin layer 18 adhered to the second layer 14 opposite the first layer 12, to form an outer skin which adds strength and scratch resistance to the film 10. The skin layer 18 is preferably formed from homo and copolymers of polypropylene, more preferably polypropylene polymers modified by rubber. Such polymers would include those sold by Mitsui under the trade name Admer™. The skin layer 18 preferably has a thickness within a range of from about 0.0001 inches to about 0.002 inches, and more preferably 0.0005 inches. The skin layer could also be composed of a polyethylene.

Figure 4:
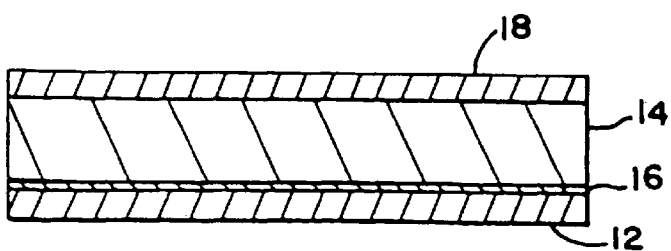
FIG. 4 is a cross-sectional view of a four-layer, gas-permeable, flexible film of the invention.
Figure 5:
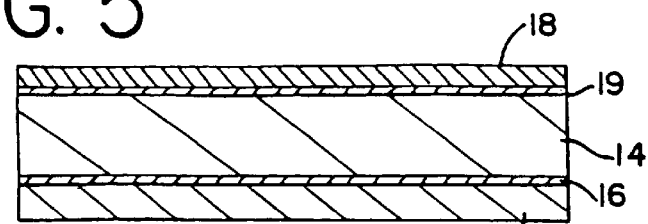
FIG. 5 is a cross-sectional view of a five-layer, gas-permeable, flexible film of the invention.

FIG. 5 shows the film of FIG. 4 except with a second tie layer 19 interposed between the skin layer 18 and the substrate layer 14 to adhere the skin layer 18 to the substrate layer 14. The second tie layer 19 may be composed of similar components as identified for the first tie layer such as modified polyethylenes.

II. Construction of the Film and its Physical Characteristics

In forming the film 10 of FIG. 1, the ultra-thin layer of polystyrene 12 is co-extruded on the substrate layer 14 using a typical feedblock co-extrusion method.

The resultant film 10 should have a flexural modulus preferably within the range of 5,000–300,000 psi, more preferably within the range of 10,000–200,000 psi, and most preferably 10,000–30,000 psi as measured in accordance with ASTM D 790. The film should have an oxygen permeability within the range of 7–30 Barrers, more preferably 8–20 Barrers, and most preferably 9–15 Barrers. A Barrer has units of (volume of gas in cm$^3$) (film thickness in cm) $(1\times10^{-10})$/(time in seconds) (surface area of film in cm$^2$) (partial pressure of gas in cm of Hg). The film should have a carbon dioxide permeability within the range of 40–80 Barrers. The film should have a nitrogen permeability of 10–100 Barrers. The film 10 should have a water vapor transmission rate of not more than 20 (g mil/100 in$^2$/day). Preferably the film should have an optical clarity within the range of about 0.1%–10% as measured by a Hazometer in accordance with ASTM D1003. The containers must also be capable of withstanding radiation sterilization at radiation levels commonly used in the industry for sterilization.

III. Fabrication of Flexible, Gas Permeable Cell Culture Containers

We turn now to the gas-permeable, flexible cell culture container (20, FIG. 2) formed from the multi-layer films described above. The cell culture container 20 includes a body 21 that is constructed from a first side wall 22 and an second side wall 24. The side walls 22 and 24 are sealed along their edges to define a containment area 26 for containing the cell culture media and cells. The side walls 22 and 24 may be sealed by any conventional means such as using heated die and platen which may be followed by a chill die and platen as is well known in the industry. Also, the side walls 22 and 24 may be sealed using inductive welding which also is known in the industry. For containers constructed from films having as the substrate layer 14 the polymer alloy including the dimer fatty acid polyamide, radio frequency techniques may be used. However, the present invention should not be construed to be limited to using any one of these fabrication techniques unless otherwise specified in the claims.

It is possible to construct various flexible, gas permeable containers from the above film in conjunction with other materials.

A. The Non-Adherent Cell Culture Container

Figure 6:
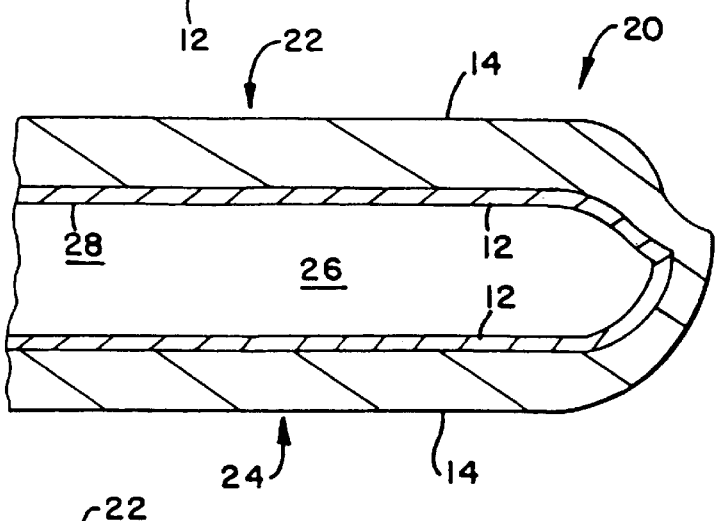
FIG. 6 is a cross-sectional view of a flexible, gas permeable container for the growth of non-adherent cells.

FIG. 6 shows a flexible, gas permeable cell culture container 10 especially useful for the growth of non-adherent cells. The container 10 is constructed from folding and sealing the film shown in FIG. 1 to define a containment area 30. The first layer of polystyrene faces the containment area 30.

B. The Hybrid Cell Culture Bag

Figure 7:
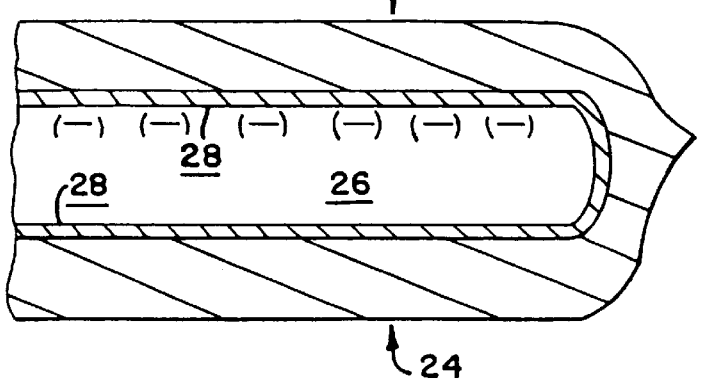
FIG. 7 is a cross-sectional view of a flexible, gas permeable container for the growth of both adherent and non-adherent cells.
Figure 7A:
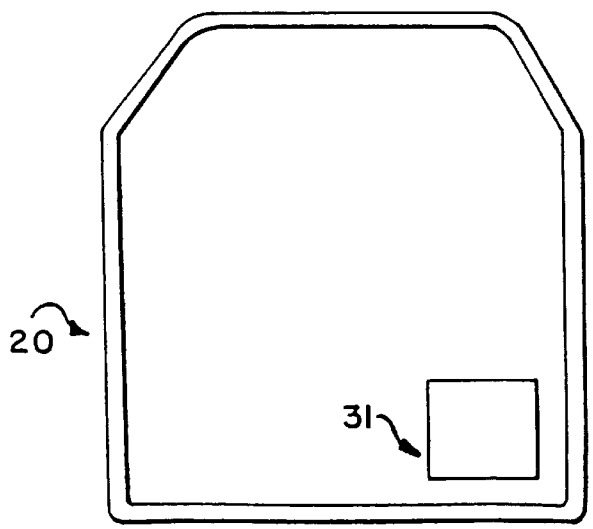
FIG. 7a is a plan view of the container of FIG. 7 showing a geometric indica to distinguish the adherent side from the non-adherent side.

FIG. 7 shows a flexible, gas permeable cell culture container 10 which is suitable for the growth of both adherent and non-adherent cell types. This container is essentially the same as the container set forth in FIG. 6 except the first side wall 22 inner surface 28 is charged with an electrostatic charge of greater than 40 dynes/cm and preferably about 60 dynes/cm. The first side wall 22 with the charge is suitable for growing adherent cells and the second side wall 24 is suitable for growing non-adherent cells. It is desirable to use some indicia 31 to indicate the charged side from the uncharged side such as the perimeter geometry of the cell culture container (See FIG. 7a). This would include such structural features as a rounding of corners or notching any portion the container, or in any way of varying the shape or structural features of the container to indicate the charged side from the uncharged side. It is also possible to have a raised or embossed area on one side of the container. It is also possible to use color coding or other printed indicia for distinguishing the charged and uncharged sides 22 and 24.

C. Non-Adherent Cell Culture Container with a Clear Panel

Figure 8:
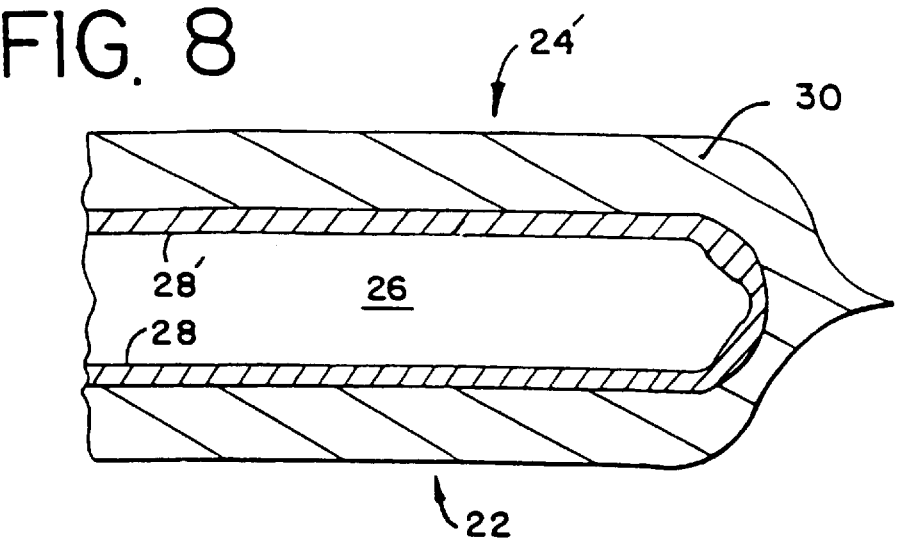
FIG. 8 is a cross-sectional view of a flexible, gas permeable container for the growth of non-adherent cells having a clear panel for inspection of the contents; and, FIG. 9 is a plan view of a flexible, gas permeable container of the present invention having access ports.

FIG. 8 shows a flexible, gas permeable cell culture container having a first side wall 22 constructed from the film shown in FIG. 1. The second side wall 24' is constructed from a film having a substrate 30 of ethylene vinyl acetate having a vinyl acetate content of 18%±2% and an inner layer 32 of HIPS. The first and second side walls 22 and 24' are bonded along their edges as set forth above or by any suitable method. The second side wall 24' has an optical clarity as measured by a Hazometer in accordance with ASTM D1003 within the range of 0.1%–10% which provides for ease of viewing the cells using a microscope or with the naked eye. The first side wall 22 would serve as the cell growth surface for non-adherent cells. It is also possible to apply an electrostatic charge to the inner surface 28 of the side wall 22 to provide for a growing surface for adherent cells.

Figure 9:
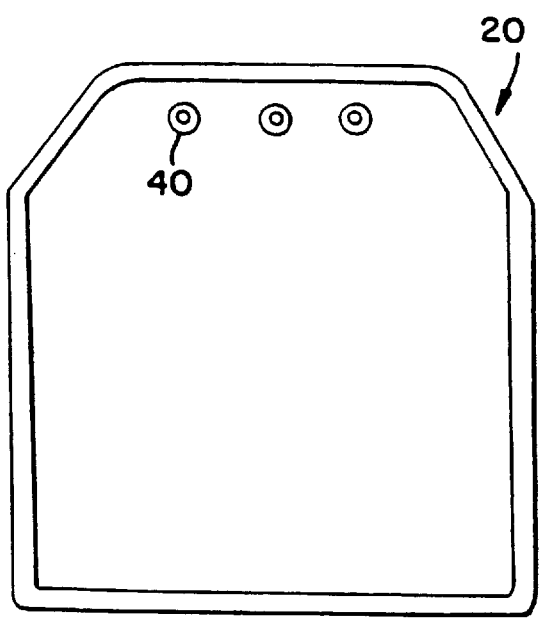

Preferably each of the containers 20 shown in FIGS. 6–8 will include access ports 40 as shown in FIG. 9. The access ports 40 facilitate filling and emptying of the container 20 of cells or cell culture media without interrupting the closed system. Of course, any number of access ports can be provided as well as a tube set assembly, or the like.

D. Other Containers

It is also desirable to construct containers using the films shown in FIGS. 3–5.

IV. Method of Providing Adjustable Gas Permeability

It is desirable to construct a flexible cell culture container 10 having a predetermined gas permeability. The predetermined gas permeability selected promotes cell growth within the container 10. Preferably, the selected permeability optimizes cell growth.

The gas permeability depends upon the types of polyolefin second layer, the thickness of the individual layers, and the overall thickness of the film.

Thus, the method of constructing or fabricating a gas permeable, cell growth container having a predetermined gas permeability comprises the following steps: providing a polystyrene, providing an appropriate polyolefin substrate layer, and coextruding the polystyrene and the polyolefin producing a layered film having a gas permeability to effect cell growth. Preferably, the cell growth will be optimal.

EXAMPLE 1

A film in accordance with the present invention was coextruded from a 0.0003 inch thick layer of polystyrene (K-resin, HIPS) on a 0.0075 inch thick layer of polyolefin alloy (PL-732®). A portion of the film was corona discharge treated. The film was formed into a flexible container or bag using a heat seal process. A length of film was cut from a roll of coextruded film. Port fitments, described in the commonly assigned U.S. Pat. No. 4,327,726, which is incorporated herein by reference, were heat sealed to the film near the midpoint of the length. The film was folded across the width of the sheet, near the sealed port fitments. The folded sheet with port fitments was placed on a heated brass platen and heat sealed using a heated brass die. The die and platen were operated at a constant temperature, the die at 280° F., and the platen at 370° F. No chilling dies or devices were employed. After sealing the container, the container was removed from the platen and allowed to air cool. Port closures were solvent bonded to the port fitments as is known in the art.

The bags were radiation sterilized and employed in cell culture studies of human progenitor cells. The bags were used to culture progenitor cells in a 10–12 day period in vitro culture. Progenitor cells were derived from purified CD34+ cells (stem cells) collected from peripheral blood as mobilized stem cells during a leukopheresis procedure. The cells were cultured via a process described in co-pending and commonly assigned patent application Ser. No. 07/855,295 which is incorporated herein by reference. Coextruded cell culture bags were seded at a cell density of $0.1-1\times10^5$ (cells/ml). Coextruded culture bags were able to support an increase in the total number of viable cells during the 10–12 day culture period. Typical increases of 40–70 fold were observed. Cell proliferation in excess of 100 fold has been obtained in the culture bags using recombinant growth factors known to support progenitor cell growth in vitro. In addition to the increase in cell number, the culture bags were able to support an increase in Colony Forming Cells ("CFC") and early granulocytes as determined by flow cytometry and cytological staining.

It is understood that, given the above description of the embodiments of the invention, various modifications may be made by one skilled in the art. Such modifications are intended to be encompassed by the claims below.

What is claimed is:

1. A multi-layer, flexible, gas-permeable film suitable for forming a cell culture container, the film comprising:
   a first layer composed of a polystyrene having a thickness within the range of 0.0001 inches to about 0.0010 inches, the first layer defining an inner cell growth surface; and,
   a second outer layer adhered to the first layer composed of a polymer alloy blend having multiple components, the second layer having a thickness within the range of 0.004 inches to about 0.015 inches.

2. The film of claim 1 wherein the polystyrene of the first layer is modified by polybutadiene rubber.

3. The film of claim 1 wherein the first layer has a thickness in the range of about 0.0002 inches to about 0.0006 inches.

4. The film of claim 1 wherein the first layer has a thickness of about 0.0003 inches.

5. The film of claim 1 wherein the polymer alloy has three components, a first component is a styrene-ethylene-butadiene-styrene block copolymer, a second component is ethylene vinyl acetate, and a third component is polypropylene.

6. The film of claim 5 wherein the styrene-ethylene-butadiene-styrene block copolymer constitutes 40 to 85% by weight of the polymer alloy, the ethylene vinyl acetate constitutes 0 to 40% by weight of the polymer alloy, and the polypropylene constitutes 10 to 40% by weight of the polymer alloy.

7. The film of claim 1 wherein the polymer alloy has four components.

8. The film of claim 7 wherein the four component polymer alloy has a first component of a polypropylene, a second component selected from the group consisting essentially of an ultra low density polyethylene and polybutene-1, a third component of a dimer fatty acid polyamide, and a fourth component of a styrene-ethylene-butadiene-styrene block copolymer.

9. The film of claim 8 wherein the first component constitutes within the range of 30–60% by weight of the polymer alloy, the second component constitutes within the range of 25%–50% by weight of the polymer alloy, the third component constitutes within the range of 5%–40% by weight of the polymer alloy, and the fourth component constitutes 5%–40% by weight of the polymer alloy.

10. The film of claim 1 further comprising a tie layer interposed between the first and second layers, the tie layer providing adhesive compatibility between the first and second layers.

11. The film of claim 10 wherein the tie layer is composed of a gas permeable olefin.

12. The film of claim 11 wherein the gas permeable olefin is an ethylene polymer containing vinyl acetate within the range of 16%–32% by weight.

13. The film of claim 12 wherein the ethylene vinyl acetate has a vinyl acetate content of 28% by weight.

14. The film of claim 1 further comprising a skin layer adhered to the second layer opposite the first layer, the skin layer providing additional strength and scratch resistance.

15. The film of claim 14 wherein the skin layer is composed of polypropylene.

16. The film of claim 14 wherein the skin layer is composed of polyethylene.

17. The film of claim 14 wherein the skin layer has a thickness within the range of 0.0001 inches to about 0.002 inches.

18. The film of claim 17 wherein the skin layer has a thickness of about 0.0005 inches.

19. The film of claim 1 wherein the first layer has an electrostatic charge greater than 40 dynes/cm.

20. A multi-layer, flexible, gas-permeable film suitable for forming a cell culture container, the film comprising:
   a first layer composed of a polystyrene having a thickness within the range of 0.0001 inches to about 0.0010 inches, the first layer defining a cell growth surface;
   a second layer adhered to the first layer composed of a polymer alloy blend having multiple components; and,
   wherein the film having physical properties within the range:
   a>10,000 but <30,000
   b>9 but <15
   c>40 but <80
   d>10 but <100
   e<20
   wherein:
      a is the flexural modulus in psi of the film measured according to ASTM D-790;
      b is the oxygen permeability in Barrers;
      c is the carbon dioxide permeability in Barrers;
      d is the nitrogen permeability in Barrers; and
      e is the water vapor transmission rate in (g mil/100 in $^2$/day).

21. The film of claim 20 wherein the film has an optical clarity within the range of 0.1%–10% as measured by a Hazometer under ASTM D1003.

22. The film of claim 20 wherein the polymer alloy has three components, a first component is styrene-ethylene-butadiene-styrene block copolymer, a second component is ethylene vinyl acetate, and a third component is polypropylene.

23. The film of claim 22 wherein the styrene-ethylene-butadiene-styrene block copolymer constitutes 40%–85% by weight of the polymer alloy, the ethylene vinyl acetate constitutes 0 to 40%% by weight of the polymer alloy, and the polypropylene constitutes 10 to 40% by weight of the polymer.

24. The film of claim 20 wherein the second layer is composed of a four component polymer alloy.

25. The film of claim 24 wherein the four component polymer alloy has a first component of a polypropylene, a second component selected from the group consisting essentially of an ultra low density polyethylene and polybutene-1, a third component of a dimer fatty acid polyamide, and a fourth component of a styrene-ethylene-butadiene-styrene block copolymer.

26. The film of claim 25 wherein the first component constitutes within the range of 30–60% by weight of the polymer alloy, the second component constitutes within the range of 25%–50% by weight of the polymer alloy, the third component constitutes within the range of 5%–40% by weight of the polymer alloy and the fourth component constitutes 5%–40% by weight of the polymer alloy.

27. A cell culture container comprising a first and second side wall each having an interior surface that cooperate to define a containment area, wherein at least the first side walls composed of a film of any of claims 1–26.

28. The container of claim 27 wherein the polystyrene first layer faces the containment area.

29. A flexible, gas-permeable cell culture container suitable for culturing cells, the container comprising:
   a first and second side wall each having edges, the first and second side walls being sealed together at their respective side wall edges to provide a containment area, wherein at least the first side wall is composed of a first layer of polystyrene having a thickness within the range of 0.0001 inches to a out 0.0010 inches the first layer facing an interior of the container to define a cell growth surface, and, a second layer adhered to the first layer of a polyolefin, the second layer having thickness within the range of 0.004 inches to about 0.015 inches.

30. The cell culture container of claim 29 further comprising at least one access port for accessing the containment area.

31. A method for fabricating a multi-layered film suitable for forming a container for culturing cells comprising the steps of:

providing a polystyrene cell growth surface;

providing a polymer alloy blend having multiple components; and, coextruding the polystyrene and the polymer alloy blend producing a layered film having a gas permeability to promote cell growth.

32. The method of claim 31 wherein the polystyrene layer has a thickness within the range of about 0.0001 to about 0.0010 inches, and wherein the polyolefin layer has a thickness within the range of about 0.004 to about 0.015 inches.

33. A flexible, gas-permeable cell culture container suitable for culturing cells, the container comprising:

a first side wall of the container being suitable for growing adherent cells, the first side wall comprises a first layer of polystyrene having a thickness within the range of 0.0001 inches to about 0.0010 inches, and, a second layer adhered to the first layer of a polymer alloy having multiple components, the second layer having a thickness within the range of 0.004 inches to about 0.015 inches;

a second side wall attached to the first side wall for growing non-adherent cells; and, means associated with the container for distinguishing the first side wall from the second side wall.

34. The container of claim 33 wherein the means for distinguishing the first side wall from the second side wall is the geometry of the container.

35. A method for culturing cells comprising the steps of:

providing a flexible cell culture container having at least one side wall of a film having a first layer of a polystyrene having a thickness from 0.0001 inches to about 0.0010 inches, and a second layer adhered to the first layer of a polymeric material having a thickness from 0.004 inches to about 0.015 inches, the first layer faces an interior of the container to provide a cell growth surface;

adding to the container a cell growth medium; and seeding the container with cells to be grown.

36. The method of claim 35 wherein the second layer is a polymer alloy having multiple components.

37. The film of claim 36 wherein the polymer alloy has three components, a first component is a styrene-ethylene-butadiene-styrene block copolymer, a second component is ethylene vinyl acetate, and a third component is polypropylene.

38. The film of claim 37 wherein the styrene-ethylene-butadiene-styrene block copolymer constitutes 40 to 85% by weight of the polymer alloy, the ethylene vinyl acetate constitutes 0 to 40% by weight of the polymer alloy, and the polypropylene constitutes 0 to 40% by weight of the polymer alloy.

39. The film of claim 36 wherein the second layer is composed of a four component polymer alloy.

40. The film of claim 39 wherein the four component polymer alloy has a first component of a polypropylene, a second component selected from the group consisting of an ultra low density polyethylene and polybutene-1, a third component of a dimmer fatty acid polyamide, and a fourth component of a styrene-ethylene-butadiene-styrene block copolymer.

41. The film of claim 40 wherein the first component constitutes within the range of 30–60% by weight of the polymer alloy, the second component constitutes within the range of 25%–50% by weight of the polymer alloy, the third component constitutes within the range of 5%–40% by weight of the polymer alloy, and the fourth component constitutes 5%–40% by weight of the polymer alloy.

42. The film of claim 35 further comprising a tie layer interposed between the first and second layers, the tie layer providing adhesive compatibility between the first and second layers.

* * * * *